United States Patent [19]

Nesheim et al.

[11] Patent Number: 5,308,755
[45] Date of Patent: May 3, 1994

[54] METHOD FOR MEASURING HEPARIN

[75] Inventors: Michael E. Nesheim, Kingston; Reginald P. Manuel, Sydenham, both of Canada

[73] Assignee: Research Corporation Technologies, Inc., Tucson, Ariz.

[21] Appl. No.: 895,078

[22] Filed: Jun. 8, 1992

[51] Int. Cl.$^5$ .............................................. C12Q 1/56
[52] U.S. Cl. ..................... 435/7.4; 435/7.1; 435/968; 435/13; 436/69
[58] Field of Search ............. 435/7.1, 7.4, 13, 968; 436/69

[56] References Cited

U.S. PATENT DOCUMENTS

| | | | |
|---|---|---|---|
| 4,180,437 | 12/1980 | Collen | 435/7 |
| 4,234,682 | 11/1980 | Bartl et al. | 435/13 |
| 4,496,653 | 1/1985 | Lill et al. | 435/7 |
| 4,543,335 | 9/1985 | Sommer et al. | 436/69 |
| 4,622,389 | 11/1986 | Nagasawa et al. | 530/331 |
| 4,668,621 | 5/1987 | Doellgast | 435/13 |
| 4,849,353 | 7/1989 | Harpel | 435/7 |
| 4,851,336 | 7/1989 | Yin | 435/13 |
| 4,883,751 | 11/1989 | Gitel et al. | 435/7 |
| 4,908,314 | 3/1990 | Orthner | 435/219 |
| 4,918,001 | 4/1990 | Kolde | 435/24 |
| 4,946,775 | 8/1990 | Yin | 435/13 |
| 4,948,724 | 8/1990 | Yin | 435/13 |

OTHER PUBLICATIONS

Nordenman et al Thrombosis Research 17, 595–600 (1980).
Walsh *Enzymatic Reaction Mechanisms* 1979 W. H. Freeman and Company pp. 86–89.
Harpel et al Ann. N.Y. Acad. Sci. vol. 485 (1986) pp. 184–198.
Sigma Catalogue 1992 Sigma Chemical Corp. p. 2115.
Vinazzu et al Thromb Res. 48 (2) (1987) pp. 153–160, Abstract only.
Purich (1983) Contemporary Enzyme Kinetics, Academia Press, pp. 1–31.
Nesheim (1983) A Simple Rate Law . . . J. Biol. Chem 258: 14708–14717.
Nesheim et al (Feb. 1989) Abstract 4709 J. Cell Biol. Abstract of Joint Meeting.
Stryer (1981) Biochemistry, W. H. Freeman, SF, pp. 110–122.
Tinoco et al (1978) Physical Chemistry, pp. 259-31-1–314.

*Primary Examiner*—Esther L. Kepplinger
*Assistant Examiner*—Lora M. Green
*Attorney, Agent, or Firm*—Scully, Scott, Murphy & Presser

[57] ABSTRACT

A method for assaying body fluid samples containing heparin and a diagnostic kit are described. Since the reactions go to completion, timing of the assay is not required. The sample is mixed with a heparin-dependent protease inhibitor and either a heparin-independent irreversible inhibitor or a protease substrate. The coagulation enzyme (protease) is then added in a limiting quantity and it either distributes between the heparin-dependent inhibitor and the heparin-indepedent irreversible inhibitor, or the heparin-dependent inhibitor and the protease substrate. The distribution pattern of complex formation of the protease with the two inhibitors or the level of product of the protease-catalyzed hydrolysis of the substrate are used as measures of the heparin activity. The irreversible inhibitor is a peptidyl chloromethyl ketone and the substrate is a synthetic chromogenic or fluorogenic compound that produces a readily measured signal.

4 Claims, 4 Drawing Sheets

METHOD FOR MEASURING HEPARIN

FIELD OF INVENTION

This invention relates to a method for measuring the anti-coagulant activity of heparin in plasma or samples of other body fluids.

BACKGROUND OF INVENTION

Heparin is widely used clinically where immediate anti-coagulation of the blood is required. Clinical situations which call for the use of heparin include, but are not limited to, myocardial infarction, deep vein thrombosis, embolism and pre and post operation in hip replacement therapy. Dosages can vary from 10,000–100,000 USP units/24 hours, leading to plasma levels ranging from 0.2–0.8 u/ml. Optimal use of heparin requires accurate measurement of plasma levels and currently two general approaches are available. It will be appreciated by those skilled in the art that heparin, as commercially supplied as an anti-coagulant, is a mixture of oligosaccharides of varying molecular weights, each consisting of repeating units of glucuronic or iduronic acid and glucosamine variously N- and O-sulfated. These components function as catalysts in the inactivation of coagulation serine protease enzymes, particularly thrombin and Factor Xa. The mechanism of inactivation differs with the two enzymes, and thus some components of heparin are active against both, whereas others of low molecular weight are selective only for Factor Xa. If one tests for heparin by measuring the prolongation of plasma clotting, the results reflect global heparin activity but do not measure activity against one specific enzyme. While such tests are easy to perform they are not very sensitive or specific. If, on the other hand, measurements are made on the basis of residual levels of purified Factor Xa after incubation of it for a carefully timed period (e.g. 30 seconds) with the test sample plus anti thrombin III or heparin cofactor II, together with a second timed interval to measure residual Factor Xa with a synthetic substrate, activities specifically directed against Factor Xa can be measured. This latter approach yields a measure of activity directed specifically at Factor Xa, but requires careful timing for accurate results to be obtained.

OBJECT OF THE INVENTION

One object of the present invention is to provide a novel assay for heparin which is more precise, more sensitive and less subject to interference than currently available assays, and can be used to specifically measure activities directed against both thrombin and Factor Xa.

It is another object of the invention to provide an assay kit for carrying out the novel heparin assay.

BRIEF STATEMENT OF INVENTION

By one aspect of this invention there is provided a a method for measuring anti-coagulant activity of heparin, comprising:

(a) mixing a sample containing heparin with a heparin-dependent irreversible inhibitor for a selected enzyme and a heparin-independent irreversible inhibitor of said enzyme;

(b) distributing a limiting quantity of said enzyme totally between said heparin-dependent irreversible enzyme inhibitor and said heparin-independent irreversible inhibitor of said enzyme so as to provide inhibitor-enzyme complexes; and (c) measuring the level of one or both said complexes produced as a measure of heparin activity present in said sample.

By another aspect of the invention there is provided a method for measuring anti-coagulant activity of heparin comprising:

(a) mixing a sample containing heparin with a heparin dependent irreversible inhibitor of a selected enzyme and a substrate of the enzyme;

(b) adding a limiting quantity of the enzyme so that it is totally inactivated by said heparin dependent enzyme inhibitor in a finite time, during which time a portion of said substrate is converted to a determinable product; and (c) determining the level of said product as a measure of heparin activity present in said sample.

By yet another aspect of the invention there is provided a diagnostic kit for determining anti-coagulant activity of heparin in a sample, comprising synergistic amounts of:

(a) a selected coagulation enzyme;

(b) an irreversible heparin-dependent inhibitor for said coagulation enzyme; and at least one of (c) an irreversible heparin-independent inhibitor for said coagulation enzyme and (d) a substrate of said coagulation enzyme.

DETAILED DESCRIPTION OF PREFERRED EMBODIMENTS

Figure 1:
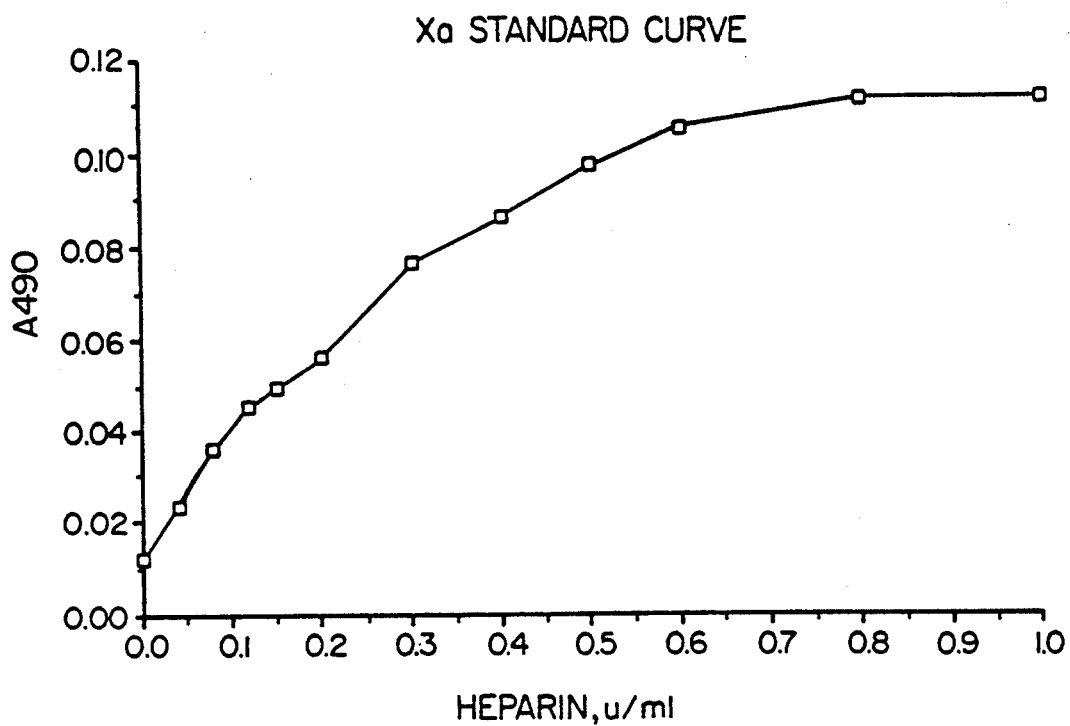
FIG. 1 is a standard curve of heparin activity against Factor Xa in a plasma sample.
Figure 2:
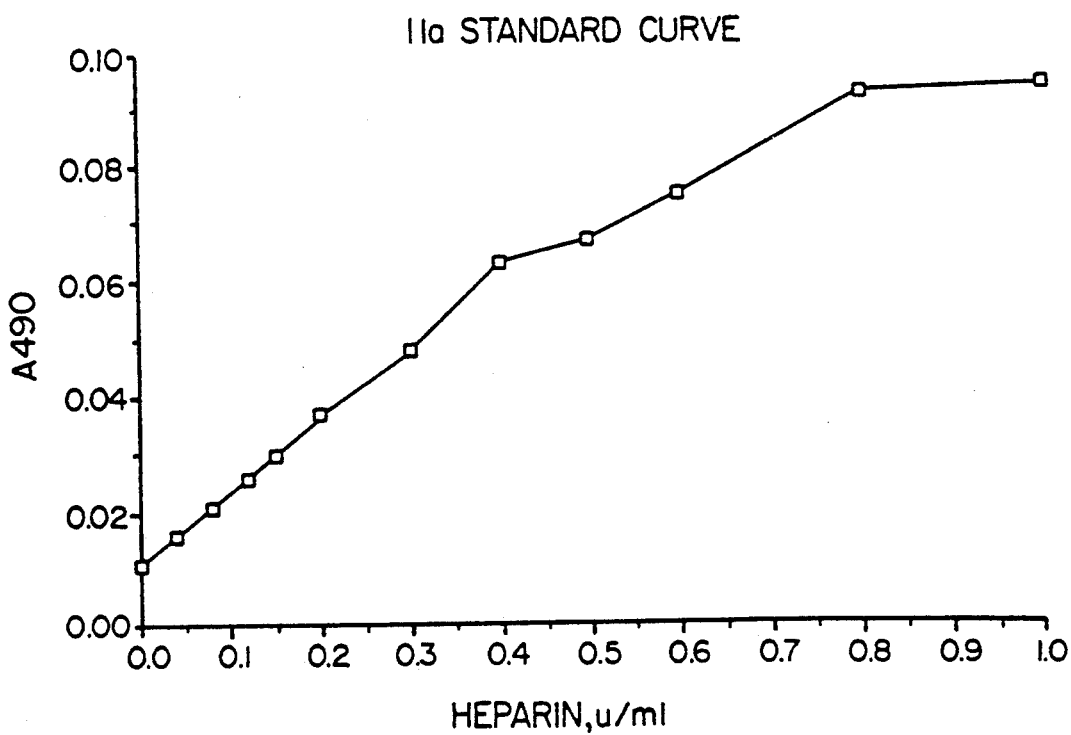
FIG. 2 is a standard curve of heparin activity against thrombin in a plasma sample.

The assays of the present invention are based on purified coagulation factors, such as thrombin or Factor Xa, in competing reactions between a heparin dependent irreversible inhibitor such as a protease and more specifically antithrombin III or heparin cofactor II plus heparin and a heparin-independent irreversible inhibitor for the enzyme such as highly specific peptidyl chloromethyl ketone inhibitors of Factor Xa or thrombin, or chromogenic or fluorescent substrates of the two enzymes. Peptidyl para-nitroanilide chromogenic substrate is a preferred substrate. The enzymes are used in limiting quantities that is to say they are completely consumed during the course of the measurements through the competing reactions. The extent to which the enzymes are consumed by each of the two different pathways is determined by the heparin levels. Thus, the measurement of the stable levels of end products at completion of the reactions provides a measure of heparin activity. No timing is required as the reactions go to completion.

When chloromethyl ketone inhibitors are used in the assay, the end products, i.e. Factor Xa/antithrombin III complex or thrombin/antithrombin III complex can be measured by standard assay techniques utilizing antibodies against antithrombin III and either Factor Xa or thrombin. When chromogenic or fluorogenic substrates are used, the final level of colour fluorescence developed is inversely proportional to the heparin activity, and no antibodies are required for the measurements.

The assays may be summarized as follows:

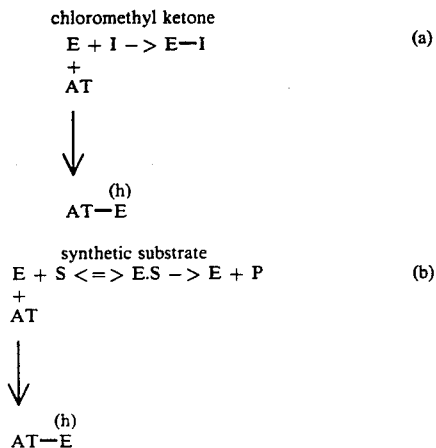

where E=enzyme (Factor Xa or thrombin); AT=antithrombin III; h=heparin; I=chloromethyl-ketone irreversible inhibitor; S=chromogenic substrate; and P=coloured product of the reaction catalyzed by the enzyme. In both schemes E is eventually consumed entirely. The amount of AT-E formed in (a) and the amount of P in (b) are influenced by heparin. Thus the convenient measurement of AT-E or P provides a measure of heparin activity. Since E is totally consumed, final levels of AT-E or P are stable and no timing of the reactions is required.

In the following examples the materials used were obtained as follows:

Human proteins Factor Xa (Xa) and thrombin (IIa) were prepared by previously published methods of Bajaj,S.P. et al (Prep. Biochem. 1983,(13), 191–214) and human anti-thrombin III was prepared according to Damus, P. S. and Rosenberg, R. D. (1976) Methods in Enzymology 45, 653–668. The plasma for the standards was from a normal human pool and was frozen at −70° C. until use. A series of 21 plasmas from patients on heparin therapy was obtained from the clinical laboratory at Kingston General Hospital. The various heparins used were Hepalean (1,000 USP units/ml, Organon Canada Ltd., Toronto, Ontario, Canada), Allan and Hanburys (10,000 USP units/ml, Glaxo Canada) and Lipohepin (20,000 USP units/ml, Riker Laboratories Inc., California). The chloromethyl ketones (CMK) Phe-Pro-Arg-$CH_2Cl$ and DansylGlu-Gly-Arg-$CH_2Cl$ (PPAck and dEGR*CMK) were from BehringCalbiochem, San Diego, Calif. Bovine Serum Albumin (BSA) was obtained from Boehringer Mannheim Canada (Dorval, Quebec). The Factor Xa and the Thrombin-specific chromogenic substrates, S-2222 and S-2238 were obtained from KabiVitrum (Helena Laboratories, Mississauga, Ontario). All other reagent grade chemicals were obtained from Sigma and BDH. The Elisa assays were done in 96 well microtitre plates from Falcon and read in a TiterTek Twinreader plate reader from Flow Laboratories (ICN Biomedicals, Mississauga, Ontario). Antisera containing polyclonal antibodies to the human proteins Prothrombin (Factor II), Factor X and antithrombin III (ATIII) were prepared using standard procedures according to the method of Hurn, B. A. L., Chantler, S. M. "Production of Reagent Antibodies", in Van Vanakis, H., Langone, J. J. (ed.): Methods in Enzymology, vol. 70. San Diego, Calif., Academic, 1980, page 104. The human proteins prothrombin (Factor II), Factor X and antithrombin III, approximately 10 mg each, were dialyzed vs. 1 liter of 0.1M citrate, pH6.5 at 4° for two hours. CL-4B Sepharose (Pharmacia) approximately 5.0 ml, was washed with 500 ml of 2.0M $Na_2CO_3$ in a Buchner funnel under aspirator vacuum using ice to keep the temperature close to 4°. The CL-4B Sepharose was resuspended in the funnel in 5–10 ml ice cold 1.0M $Na_2CO_3$ and cyanogen bromide (0.5 gm dissolved in 1.0 ml acetonitrile) was added and mixed. One minute later the fluid was removed under vacuum and the activated CL-4B. Sepharose was then washed under vacuum with 0.1M citrate, pH 6.5, (approximately 500 ml). The cake of activated CL-4B Sepharose was then added to the dialyzed protein and the mixture was gently stirred at 4° overnight. The CL-4B Sepharose-protein conjugate was then placed in a Buchner funnel and washed under vacuum with 0.1M citrate, pH 6.5, approximately 250 ml. To block any remaining coupling sites, the CL-4B Sepharose-protein conjugate was placed in a beaker with approximately 50 ml 1.0M Tris, pH 7.4, and stirred gently at 4° C. overnight. The CL-4B Sepharose-protein conjugate was then stacked into a 10 cc column, washed with 0.02M Tris, 0.15M NaCl, pH 7.4 (TBS) and stored at 4° C. Antisera containing approximately 100 mg of total immunoglobulin was diluted to 5.0 ml in TBS. This solution was applied to the appropriate CL-4B Sepharose-protein conjugate column, also equilibrated in TBS at 22° C. The column was washed with TBS until the absorbance at 280 nm was less than 0.01. The bound antibody was eluted from the column with 0.1M Glycine, 0.5 NaCl, pH 2.8, collecting 2.5 ml fractions into 1.0 ml 1.0M Tris HCl, pH 8.0. The fractions containing the affinity-purified antibodies were pooled and concentrated using 80% ammonium sulfate precipitation. The affinity-purified antibodies against prothrombin and Factor X were stored in TBS, 0.02% sodium azide. The affinity-purified antibody against antithrombin III was conjugated to horseradish peroxidase according to the method of Wilson, M. B. and Nakane, P. K. (1978) in: Immunofluorescence and Related Techniques (W. Knapp, H. Holubar and G. Wisk, eds.). Elsevier/North-Holland, Amsterdam, page 215, and was stored without azide.

EXAMPLE 1

Assay of Heparin

Assay of Heparin Activity Against Factor Xa and Thrombin Using an Immunological Detection System (ELISA)

The entire procedure for the assay was carried out at room temperature (22° C.) and in the ELISA section as noted, some parts were carried out at 4° C. for convenience. To quantify heparin in plasma, a series of standards were first tested in this system. Normal human plasma (NHP) was supplemented with known amounts of the three heparins to give sample concentrations of from 0.025, to 2.0 u/ml heparin. 10 μl heparinized plasma sample were pipetted into 5.0 ml polystyrene tubes in duplicate (one set for IIa and one set for Xa inhibition). A blank sample was included in each set and was treated in the same manner as the standards or test plasma with the exception that 10 μl plain NHP (no heparin added) was used. To each tube is added 100 μl of a solution containing antithrombin III and one of the chloromethyl ketone (CMK) inhibitors. The ATIII concentration was 0.25 μM and the CMK concentration was 0.125 μM and the buffer was 0.02M Tris HCl, 0.15M NaCl, pH 7.4(T. S.). For the measurement of activity against Factor Xa, ATIII plus dEGR CMK was used and for the measurement of activity against thrombin and ATIII+PPA-CMK was used for the IIa inhibition. To each tube was added 100 μl of the appropriate enzyme, Factor Xa or thrombin at 0.025 μM in T. S. with vortexing. The tubes were incubated for 10 minutes at room temperature and then the appropriate dilution with phosphate buffered saline (PBS)+0.05% Tween®-20 (PBS-Tween) was made for the ELISA plate. The samples were diluted 1/25 and the samples to measure activity against Factor Xa were diluted 1/100.

For the ELISA section of the assay, PCV microtitre plates (Falcon TM) were coated with sheep anti-human II or rabbit anti-human Factor X antibodies at 10 μg/ml, 100 ul/well, diluted in 50 mM carbonate buffer pH 9.6 for two hours at room temperature (or overnight at 4° C.). The top four rows (A-D) of the plates were coated with the anti-human II antibodies and the bottom four rows (E-H) were coated with the anti-human X antibodies for convenience since the samples to measure activities against thrombin and Factor Xa are treated exactly the same once they have been applied to the plate. After the coating antibody incubation, the wells were emptied and to each was added 200 μl PBS-BSA (PBS, pH 7.4 containing 20 mg/ml bovine serum albumin) as a blocking agent, and the plate was again incubated for 2 hours at room temperature or overnight at 4° C. The plate was emptied and washed four times with PBS-Tween 200 μl/well, and 100 μl of the diluted samples and blanks were applied to the appropriate wells. The plate was incubated at room temperature for two hours and then washed four times with PBS-Tween. The anti-ATIII-HRP conjugated antibody was diluted 1/20,000 with PBS-Tween and 100 μl added in every well followed by a two hour incubation at room temperature. The plate was then emptied, washed four times with PBS-Tween and once with water and then developed with 0.4 mg/ml 0-phenylenediamine (OPD) and 0.03% $H_2O_2$(v/v), 100 μl/well. The plates were then monitored over time at a wavelength of 450 nm with correction at 620 nm, or were incubated at room temperature for one hour. The reactions were stopped by the addition of 2.5M $H_2SO_4$ (50 ul/well). The acidified samples in one plate were read at a wavelength of 490 nm, corrected at 620 nm. Samples included standards of known heparin activities. Standard curves were generated and the activities of heparin (against both Factor Xa and thrombin) in the test plasmas were read from these standards curves.

RESULTS

Immunological Assays (ELISA)

Plasma samples supplemented with heparin at various concentrations were assayed for anti Factor Xa and anti thrombin activities of heparin by ELISA as described above. The results are shown in FIGS. 1 (anti Factor Xa) and 2 (antithrombin) where colour (A490) was plotted relative to the heparin concentrations of the plasma samples. These curves effectively represent standard curves by which to assay unknown specimens.

Figure 3:
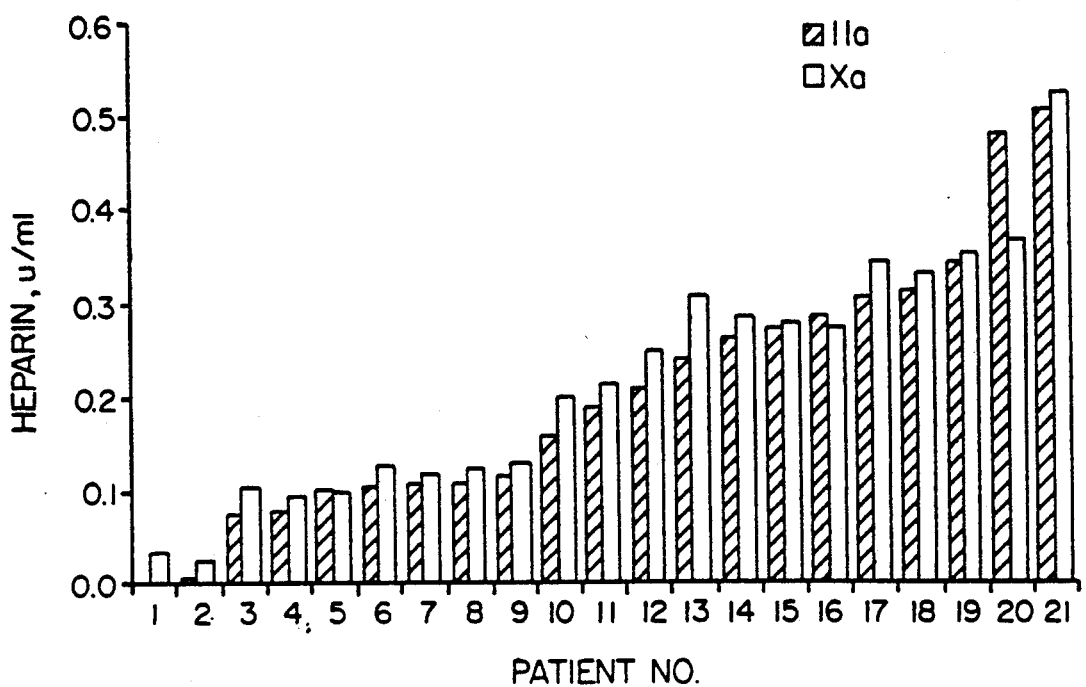
FIG. 3 is a bar graph illustrating anti Factor Xa and anti thrombin activities of heparin in clinical samples.

The activities of 21 clinical specimens were thus assayed and heparin activities were read from the standard curves. Results are represented in FIG. 3, where the open bars and the stippled bars represent anti Factor Xa and anti thrombin activities of heparin, respectively.

Figure 4:
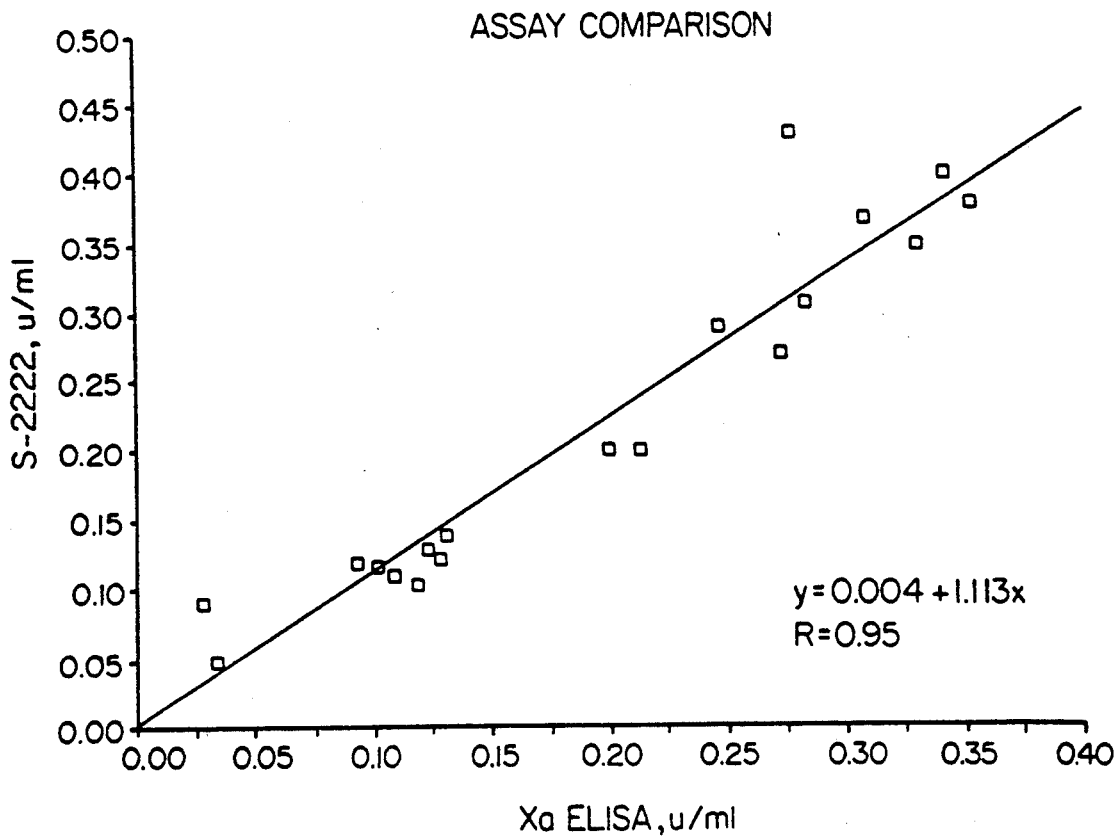
FIG. 4 is a graph comparing chromogenic results with ELISA results for heparin activity.

The anti Factor Xa activities of these specimens were also measured by an adaptation of a commercially available chromogenic heparin assay and results obtained with the ELISA and chromogenic assays were compared. The results are shown in FIG. 4, where chromogenically determined activities (vertical axis) are plotted against the ELISA results (horizontal axis). The correlation coefficient is 0.95 and the line proceeds through the origin, indicating that both assays yield the same result.

EXAMPLE 2

Assay of Heparin Activity Against Factor Xa and Thrombin with Chromogenic Substrates and Limiting Levels of Factor Xa or Thrombin Principles A limiting quantity of Factor Xa or thrombin is added to a solution of purified anti thrombin III, heparin and a Factor Xa-specific or thrombin-specific chromogenic substrate. Upon the addition of the enzyme, it simultaneously undergoes irreversible inhibition by antithrombin III plus heparin, and catalyzes cleavage of the chromogenic substrate to yield a yellow product, para-nitroanaline. Since the enzyme is present in a limiting amount, eventually all of it gets inhibited and the conversion of the chromogenic substrate ceases. The amount of coloured product generated by the time the reaction stops is therefore inversely related to the activity of heparin. Thus, all reactions are monitored until they stop, and the total concentrations of coloured product formed is measured spectrophotometrically. No timing of the reaction is required.

Solutions

Substrate: 0.535 uM purified anti thrombin III in 0.02M Tris-HCl, 0.15M NaCl, ph 7.4 plus 0.1 mM S2222 (for Factor activity against Xa) or 0.05 mM S2238 (for activity against thrombin).
Factor Xa: 0.1 uM purified human factor Xa in 0.02M Tris-HCl, 0.15M NaCl, 1% polyethylene glycol 8000.
Thrombin 0.05 uM purified human thrombin in 0.02M Tris-HCl, 0.15M NaCl, 1% polyethylene glycol 8000.

Procedure 0.90 ml substrate and 0.05 ml heparin sample was drawn into a 1.0 ml plastic spectrophotometer cuvette pipette. Baseline absorbance at 405 nm was established. The reaction was initiated with 9.5 ul of either Factor Xa or thrombin solution and the absorbance monitored at 405 nm until the reactions stopped. The difference between the absorbance before the addition of enzyme and at the end of the reactions was measured($\Delta A405$). The spectrophotometer used was a model lambda 4B from Perkin-Elmer.

Results—Chromogenic Substrate Assays

Buffer or plasma samples were supplemented with heparin and assayed for heparin with a limiting amount of enzyme and purified antithrombin III as described above. These assays are distinguished from previously available chromogenic assays in that the substrate, enzyme and inhibitors were co-incubated rather than sequentially incubated, such that the limiting amount of enzyme is eventually totally consumed. This eliminates the requirement for timed incubations and provides a measure of heparin from the terminal stable absorbance readings.

Figure 5:
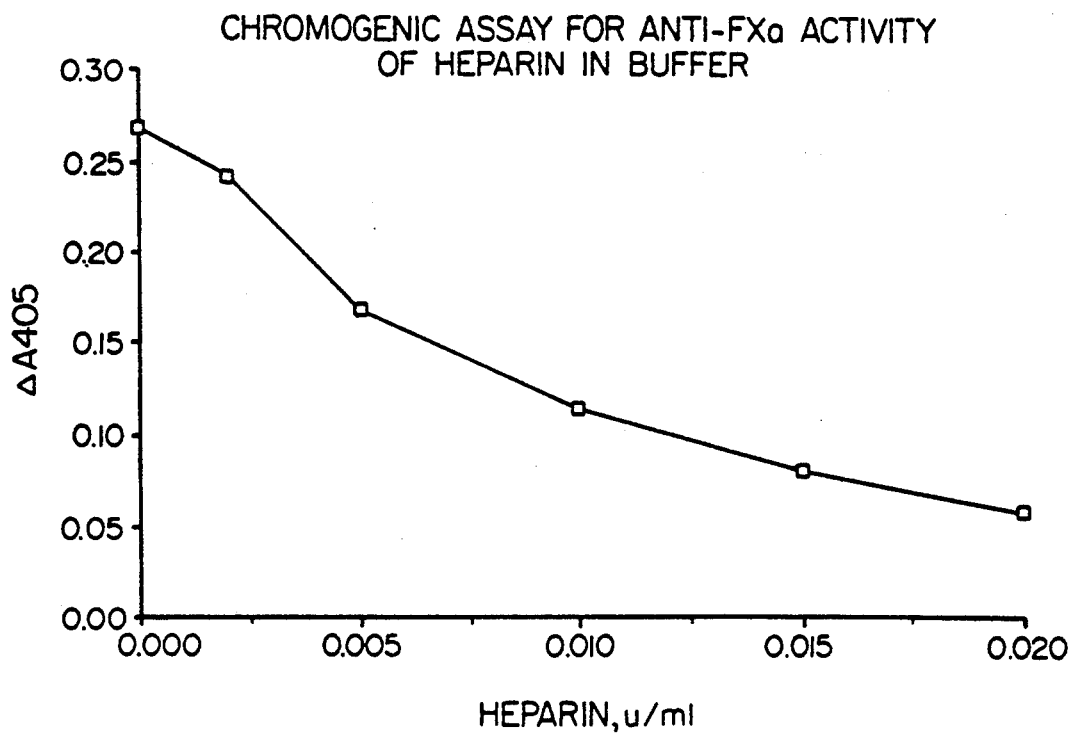
FIG. 5 is a graph illustrating a chromogenic assay for anti Factor Xa activity of heparin in a buffer.
Figure 6:
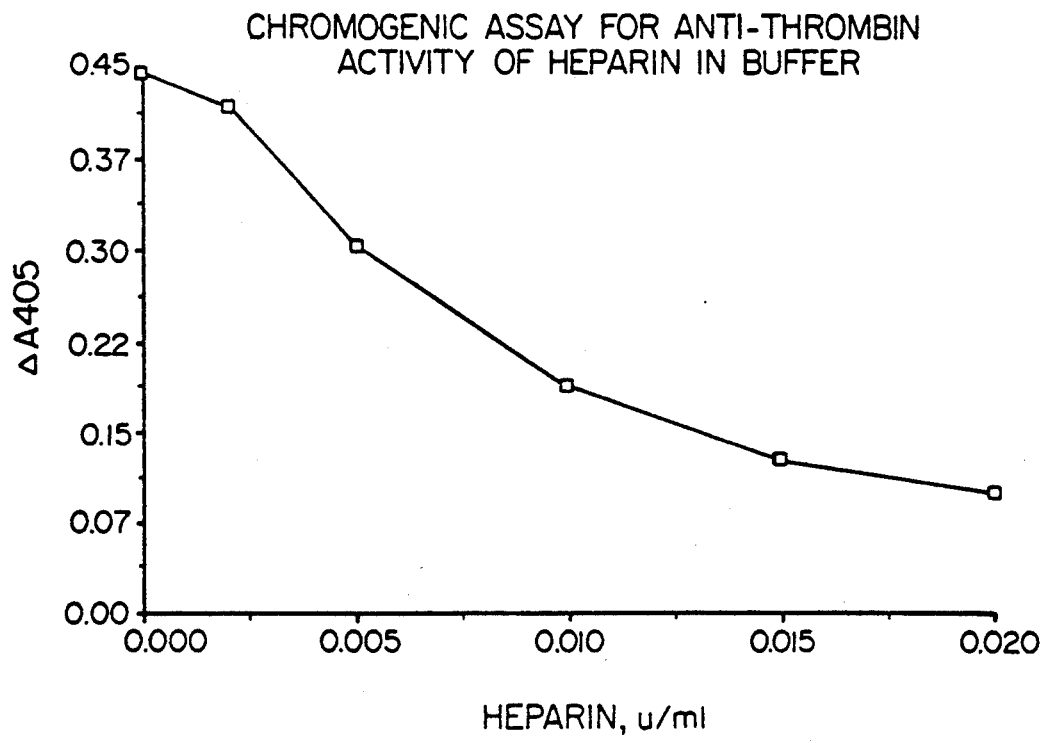
FIG. 6 is a graph illustrating a chromogenic assay for anti thrombin activity of heparin in a buffer.
Figure 7:
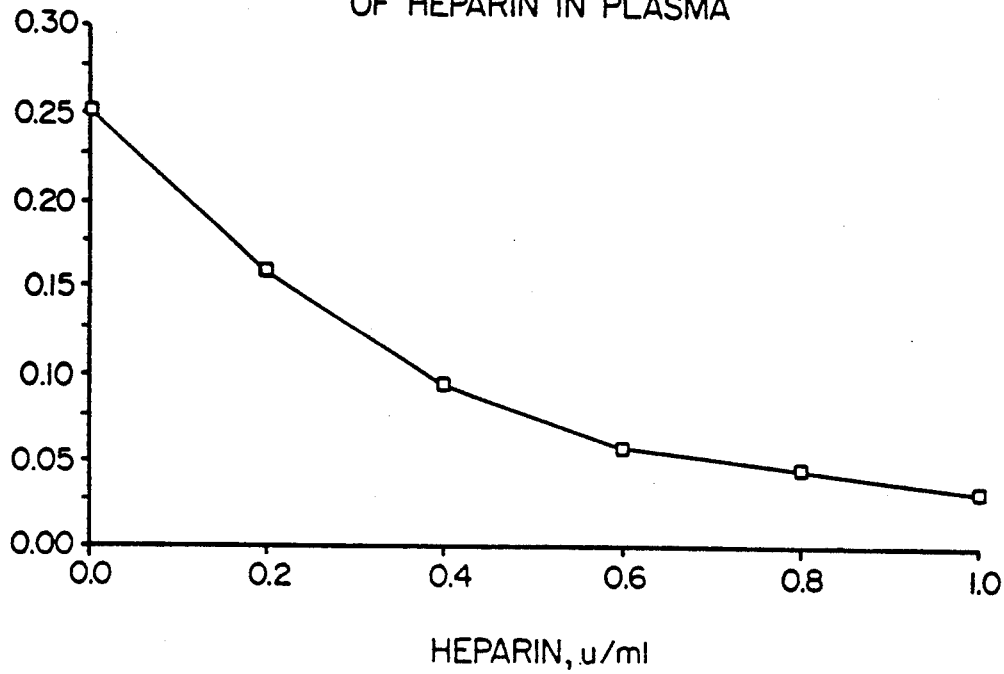
FIG. 7 is a graph illustrating a chromogenic assay for anti Factor Xa activity of heparin in a plasma sample.
Figure 8:
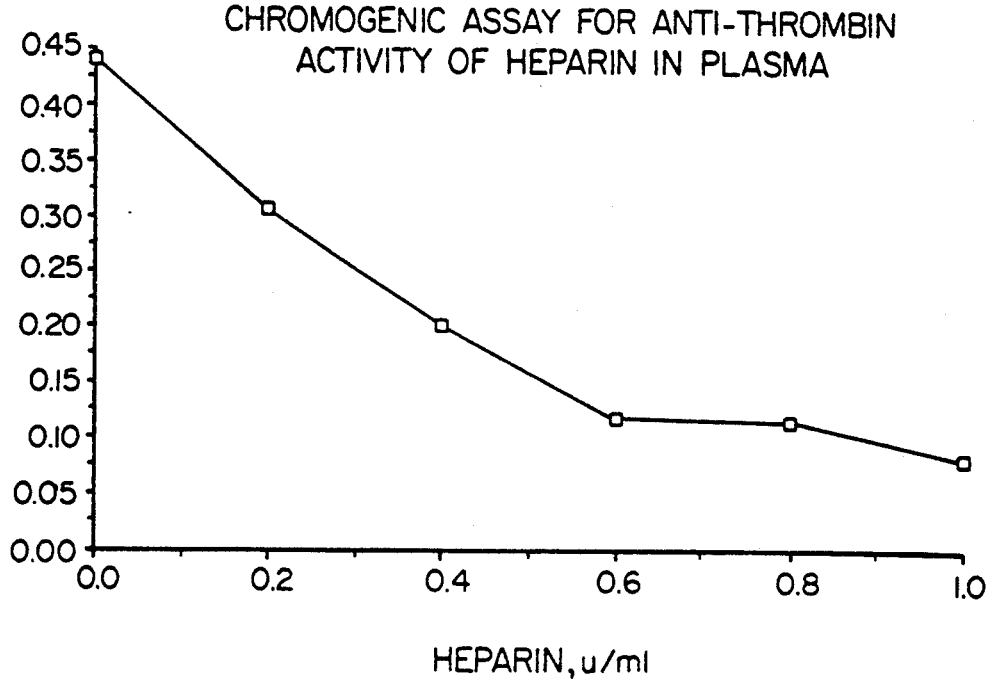
FIG. 8 is a graph illustrating a chromogenic assay for anti thrombin activity of heparin in a plasma sample.

Results with Factor Xa and Thrombin in a buffered system are shown in FIGS. 5 and 6, respectively, where ($\Delta$A405) is plotted against the final activities of heparin in the assay. The stable value was determined at 40 minutes of incubation. Similar results with plasma samples supplemented with heparin and diluted 1/100 are shown in FIGS. 7 and 8. In these figures the $\Delta$A405 is plotted against the heparin activities of the plasma samples. In both systems (buffer plus heparin or plasma plus heparin) a systematic decrease in $\Delta$A405 correlates with increasing levels of heparin and provides a conveniently standardized response.

It will, of course, be appreciated that assay kits form part of the present invention. It is contemplated that a diagnostic kit for use in a routine blood testing laboratory or the like would comprise synergistic amounts of: a selected coagulation enzyme, generally selected from thrombin and Factor Xa; and irreversible heparin dependent protease inhibitor, such as, but not limited to, antithrombin III or heparin cofactor II; and an irreversible heparin-independent inhibitor for the enzyme, such as, but not limited to, a peptidyl chloromethyl ketone inhibitor for the selected enzyme or a peptidyl para nitroanilide chromogenic substrate for the selected enzyme. Preferably, but not essentially the active components of the kit would be provided in lyopholized (freeze dried) form which could be reconstituted by addition of a buffered aqueous solution, in conventional manner.

We claim:

1. A method of measuring anti-coagulant activity of heparin in a plasma sample comprising:
   (a) mixing a plasma sample containing heparin with a heparin dependent irreversible inhibitor, selected from the group consisting of antithrombin III and heparin co-factor II, and a selected coagulation serine protease enzyme and a substrate of the enzyme, selected from the group consisting of chromogenic and fluorogenic substrates;
   (b) adding a limiting quantity of the enzyme so that is totally inactivated by said heparin dependent irreversible inhibitor in a finite time, during which time a portion of said substrate is converted to a determinable product; and
   (c) determining the level of said product as a measure of heparin activity present in said plasma sample.

2. A method as claimed in claim 1 wherein said protease is selected from the group consisting of Factor Xa and thrombin.

3. A method as claimed in claim 1 wherein said chromogenic substrate is a peptidyl para-nitroanilide substrate.

4. A method as claimed in claim 1 wherein heparin activity is measured by determining a colour level generated from said chromogenic substrate.

* * * * *

UNITED STATES PATENT AND TRADEMARK OFFICE
CERTIFICATE OF CORRECTION

PATENT NO. : 5,308,755
DATED : May 3, 1994
INVENTOR(S) : Michael E. Nesheim, et al.

It is certified that error appears in the above-indentified patent and that said Letters Patent is hereby corrected as shown below:

On the Title Page, Section [56], line 3: "12/1980" should read --12/1989--

Column 4, line 18: "4°" should read --4°C--

Column 5, line 9: "100 μl" should read --100 μℓ--

Column 5, line 26: "TM" should read --  --

Column 6, line 55: "Thrombin" should read --Thrombin:--

Signed and Sealed this

Eleventh Day of June, 1996

Attest:

BRUCE LEHMAN

*Attesting Officer*  *Commissioner of Patents and Trademarks*